United States Patent
He et al.

(10) Patent No.: US 10,441,624 B2
(45) Date of Patent: Oct. 15, 2019

(54) APPLICATION OF DIPEPTIDE AS ACE ENZYME ACTIVITY INHIBITOR

(71) Applicant: WITHYOU BIOTECHNOLOGY CO., LTD., Guangzhou (CN)

(72) Inventors: Xionglei He, Guangzhou (CN); Wei Zhu, Guangzhou (CN)

(73) Assignee: WITHYOU BIOTECHNOLOGY CO., LTD., Guangzhou (CN)

( * ) Notice: Subject to any disclaimer, the term of this patent is extended or adjusted under 35 U.S.C. 154(b) by 91 days.

(21) Appl. No.: 15/503,328

(22) PCT Filed: Aug. 11, 2014

(86) PCT No.: PCT/CN2014/084089
§ 371 (c)(1),
(2) Date: Feb. 10, 2017

(87) PCT Pub. No.: WO2016/023150
PCT Pub. Date: Feb. 18, 2016

(65) Prior Publication Data
US 2018/0207224 A1 Jul. 26, 2018

(51) Int. Cl.
*A61K 38/05* (2006.01)
*A61K 38/55* (2006.01)

(52) U.S. Cl.
CPC ............ *A61K 38/05* (2013.01); *A61K 38/556* (2013.01)

(58) Field of Classification Search
None
See application file for complete search history.

(56) References Cited

FOREIGN PATENT DOCUMENTS

| CN | 102432670 A | 5/2012 |
|----|-------------|--------|
| CN | 103736077 A | 4/2014 |

OTHER PUBLICATIONS

"Effect of Peptide-Based Captopril Analogues on Angiotensin Converting Enzyme Activity and Peroxynitrite-Mediated Tyrosine Nitration", Organic & Biomolecular Chemistry, 2011, pp. 5185-5192.

"Showing Metabocard for Cysteinyl-Alanine (HMDB28768)", http://www.metabolomicscentre.ce?utm_source=hmdb&utm_medium=banner&utm_campaign=tmic-campaign.com, Feb. 14, 2017, pp. 1-7.

Bhaskar, et al., "Synthesis, Characterization and Antioxidant Activity of Angiotensin Converting Enzyme Inhibitors", Org. Biomol. Chem, 2011, pp. 1356-1365.

Huan, "Structural Parameterization and QSAR of Two Dipeptide Inhibitor of Ace", Computers and Applied Chemistry, Aug. 2005,pp. 1-5.

Lin, "Simulating the Covalent Modification of Fe(III)-Salophen With Amino Acid Histidine or Dipeptide CYS-HIS", College of Chemistry and Chemical Engineering; University of South China, 2007,pp. 1607-1610.

Liu, et al., "OSAR Study on Ace Inhibitory Peptides Based on Amino Acids Descriptor HVHES", Acta Chemica Sinica, 2012, pp. 83-81.

Liu, "The Study of Rice Protein Inhibitory", Research on Ace Inhibitory Peptides in Rice, pp. 1-57.

Peng, "QSAR Study on Angiotension I-Converting Enzyme Inhibitory Peptides", University of Shanghai for Science and Technology Master Dissertation, Jan. 2012, pp. 1-89.

International Search Report for International Application No. PCT/CN2014/084089 dated Mar. 27, 2015.

*Primary Examiner* — Samantha L Shterengarts
(74) *Attorney, Agent, or Firm* — Michael J. Feigin, Esq.; Feigin and Fridman LLC

(57) ABSTRACT

An application of dipeptide as an ACE enzyme activity inhibitor. Virtual screening is performed on 400 types of dipeptide based on ACE inhibiting effects thereof according to a detected ACE enzyme crystal structure by using self-developed software and adopting a molecular docking method, experiments are conducted to verify the ACE inhibitory activity of the dipeptide obtained by virtual screening, and it finds out that the dipeptide with the N terminal as cysteine has better ACE inhibitory activity.

2 Claims, 2 Drawing Sheets

APPLICATION OF DIPEPTIDE AS ACE ENZYME ACTIVITY INHIBITOR

FIELD OF THE INVENTION

The present invention relates to a new application of dipeptide, and more particularly, to an application of dipeptide as an ACE enzyme activity inhibitor.

BACKGROUND OF THE INVENTION

Angiotensin converting enzyme (ACE) is a zinc metalloproteinase, and a carboxyl dipeptidase, which is one of the important proteases in the renin-angiotensin system. The ACE plays an important role in the regulation of human blood pressure. It removes His-Leu by acting on the terminal of angiotensin I to produce angiotensin II, which allows contraction of arterial smooth muscle, causing rapid rise in blood pressure. An effective method of lowering the blood pressure is inhibiting the ACE activity. Current pharmaceuticals for treatment of high pressure are mostly synthetic chemicals, which have certain adverse effects, such as cough, taste disorders, rashes and other side effects. Thus ACE inhibitory peptides prepared from food-borne proteins as raw material represent an important direction for the development of antihypertensive pharmaceuticals due to the high level of safety, low level of toxic or side effects and other advantages thereof.

Short peptides are easy to prepare, and substantially have no side effects on the human body. Researches show that, a short peptide with specific structure, for example, dipeptide, tripeptide and tetrapeptide, has certain inhibitory effect on the activity of ACE, which makes the short peptide an ACE enzyme inhibitor having a broad development prospect.

LIU Huan, LE Guowei, SHI Yonghui, et al. Structure-activity relationship of angiotensin converting enzyme dipeptide inhibitors [J]. Computers and Applied Chemistry, 2006, 22(8):631-635 discloses that a model of structure-activity relationship of angiotensin converting enzyme dipeptide inhibitors is established from the primary structures of peptide chains, by taking molecular electro-negativity edge vector (MEEV) as a parameter, and taking 36 angiotensin converting enzyme dipeptide inhibitors as samples. The rule of "distance of two, five, and seven chemical bond" inhibitory enzyme activity of dipeptide bond is obtained by means of model analysis, said rule means: (1) the carboxyl of the peptide bond forms two-ligand with Zn atom, which is stabilized by the H-bond formed between the N-atom and the carboxyl oxygen of the peptide bond; (2) the five-bond structure unit is formed between the carboxylate radical group acting with Arg (Arginine) positive charged salt bond in the ACE enzyme and the amino group of the second amino acid to play a key role in antihypertensive effect; and (3) the amino group of the peptide bond in the dipeptide inhibitor containing an aromatic amino acid shows trans configuration with the hydroxyl terminal of the benzene ring portion, with seven bonds between them.

LIU Jing, PENG Jianqiu, and GUAN Xiao. Modeling study on quantitative structure-activity relationship of angiotensin converting enzyme inhibitory peptides based on multiple linear regression [J]. Journal Analytical Science, 2012, 28(001):16-22 discloses that a multiple linear regression (MLR) model of structure and activity is established using an amino acid structure describer SVHEHS to characterize dipeptide, tripeptide and tetrapeptide sequences competitively inhibiting Angiotensin Converting Enzyme (ACE), respectively. The correlation coefficient, cross validation correlation coefficient, root mean square error and external validation correlation coefficient are respectively 0.851, 0.781, 0.327, and 0.792 for the ACE inhibitory dipeptide model; respectively 0.805, 0.717, 0.339, and 0.817 for the tripeptide model; and respectively 0.792, 0.553, 0.393, and 0.630 for the tetrapeptide model.

According to Liu Huan. Research on ACE inhibitory peptides in rice [D]. Jiangnan University, 2005, a model for structure-activity relationship of angiotensin converting enzyme dipeptide inhibitors is established by taking molecular electro-negativity edge vector (MEEV) as a parameter, and taking 36 angiotensin converting enzyme dipeptide inhibitors as samples. The model analysis shows that hydrophobic amino acids, for example, aromatic amino acids and branched-chain amino acids at C-terminal, are key factors affecting ACE inhibitory activity.

The results disclosed in LIU Jing, GUAN Xiao, PENG Jianqiu. QSAR study on ACE inhibitory peptide based on amino acid descriptor SVHEHS [J] Acta Chimica Sinica, 2012, 70(1):83-91 show that the hydrophobicity (X15), electrical property (X17), and stereoscopic feature (X24) of C-terminal amino acid, as well as stereoscopic feature (X12) of N-terminal amino acid of the dipeptide are highly correlated to the activity of the peptide.

The results disclosed in PENG Jianqiu. Research on quantitative structure-activity relationship of ACE inhibitory peptide [D]. University of Shanghai for Science and Technology, 2012 demonstrate a dipeptide model with $R^2=0.851$, RMSE=0.327, $Q^{2LOO}=0.781$, $Q^{2ext}=0.792$, and the hydrophobicity and charge property of the C-terminal amino acid residue and the stereoscopic property of the N-terminal amino acid residue have a relatively strong influence on the activity of an ACE inhibitory dipeptide, particularly, the strong hydrophobicity and weak charge property of the C-terminal amino acid residue have a positive effect on the activity of an ACE inhibitory dipeptide; and the hydrophobicity, electrical property, and stereoscopic property of C-terminal amino acid residue, and the stereoscopic property of N-terminal amino acid residue are highly correlated with the activity of a peptide.

In prior art, short peptides inhibiting ACE activity are researched from multiple perspectives in an attempt to determine the relationship between the structure of a short peptide and the ACE inhibitory activity. However, the results of the existing researches have limitations in that the accuracy of the predicted results is not high, and no dipeptide with high ACE inhibitory activity is found.

Developing a dipeptide with a high inhibitory activity is of great practical significance.

SUMMARY OF THE INVENTION

The object of the present invention is to provide an application of a dipeptide as an ACE enzyme activity inhibitor.

The above object is achieved by the technical solution of the present invention as follows.

According to the invention, virtual screening is performed on 400 dipeptides for ACE inhibitory effect based on determined ACE enzyme crystal structure using a self-developed software and a molecular docking method, and experiments are then conducted to verify the ACE inhibitory activities of the dipeptides obtained by virtual screening. It is found that a dipeptide has a relatively improved ACE inhibitory activity when the N-terminal of the dipeptide is a cysteine; and the dipeptide has even better ACE inhibitory activity when the C-terminal amino acid of the dipeptide is a basic amino acid or an aliphatic amino acid; particularly, the dipeptide has best ACE inhibitory activity when the basic amino acid is H or K, or the aliphatic amino acid is A or I.

The amino acid in the dipeptide is in L-form or D-form, and at least one amino acid in the dipeptide may be optionally modified with a group which can improve the stability of the dipeptide in vivo.

A dipeptide for inhibition of ACE enzyme activity is provided, wherein the N-terminal of the dipeptide is a cysteine, the amino acid in the dipeptide is in L-form or D-form, and at least one amino acid in the dipeptide may be optionally modified with a group which can improve the stability of the dipeptide in vivo.

Preferably, the C-terminal amino acid of the dipeptide is a basic amino acid or an aliphatic amino acid. Particularly, the basic amino acid is H or K, the aliphatic amino acid is A or I.

The present invention has the advantageous effects as follows:

The dipeptides of the present invention can inhibit the activity of ACE greatly, with an ACE inhibition rate of more than 30% at the concentration of 20 μg/ml. The inhibitory activities thereof are far beyond those of existing dipeptides. Thus, the dipeptides of the present invention have great potential for further development.

DETAILED DESCRIPTION OF THE EMBODIMENTS

The technical solution of the present invention is further described hereinafter with reference to experiments.
Determination of ACE Enzyme Activity
Kinetic Curves with Different Amounts of ACE Enzyme
Preparation for the reaction is made according to the following table:

|  | No. | | | | | |
| --- | --- | --- | --- | --- | --- | --- |
|  | 1 | 2 | 3 | 4 | 5 | 6 |
| FAPGG reagent (μl) | 200 | 200 | 200 | 200 | 200 | 200 |
| 115 u/L ACE (μl) | 20 | 16 | 12 | 8 | 4 | 0 |
| Ultrapure water (μl) | 20 | 34 | 28 | 32 | 36 | 40 |
| Note: enzyme activity | 115 u/L | 92 u/L | 69 u/L | 43 u/L | 23 u/L | 0 u/L |

The substances are mixed and placed in a SpectraMax microplate reader to determine change of absorbance value with 340 nm as a main wavelength and 405 nm as a reference wavelength at 37° C., and continuously monitored for 1 hour.

Figure 1:
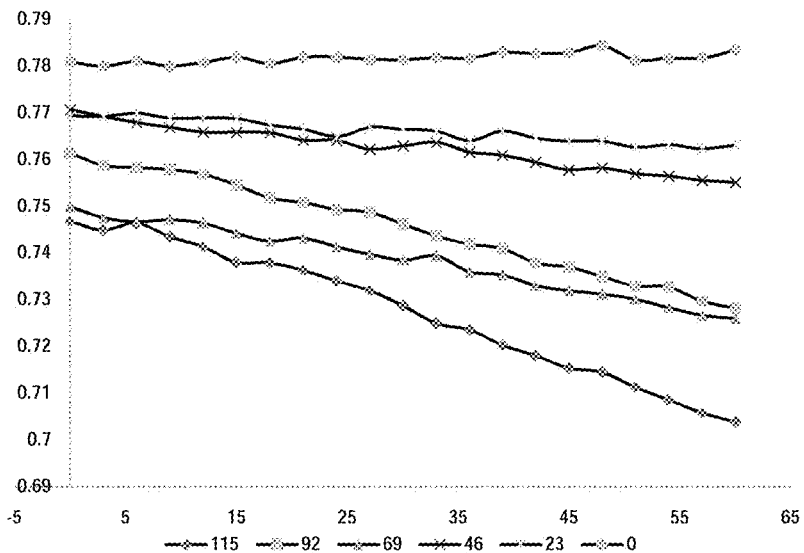
FIG. 1 is the kinetic curves with different amounts of ACE enzyme.
Figure 2:
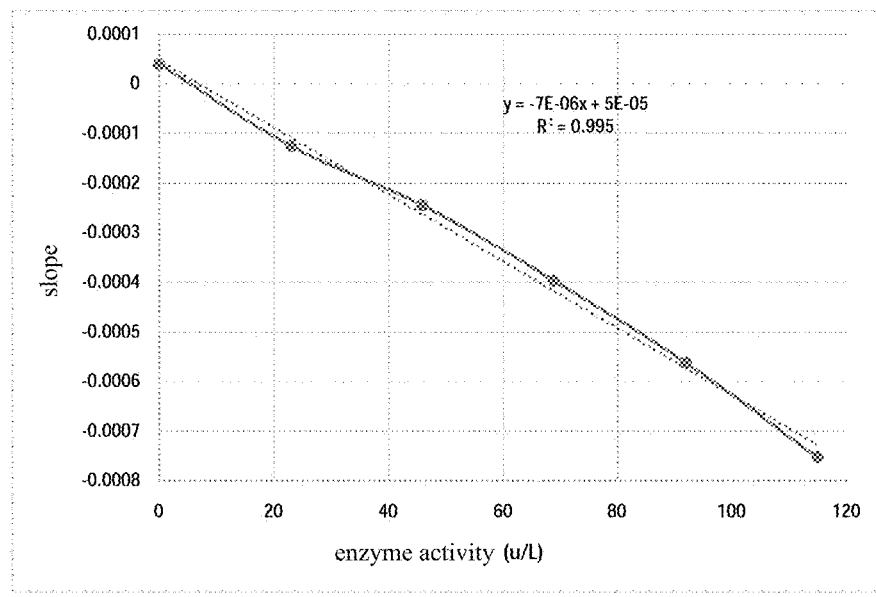
FIG. 2 is a relation curve of slope of linear segment of the kinetic curve vs enzyme activity.

The kinetic curves with different amounts of ACE enzyme are shown in FIG. 1, and the relation curve of slope of linear segment of the kinetic curve vs the enzyme activity is shown in FIG. 2. The results show that, slope of linear segment of the kinetic curve and the ACE enzyme activity are in a linear relation, with a regression equation $y=-7*10^{-6}x+5*10^{-5}$, $R^2=0.995$.

Inhibitory Effect of Different Concentrations of Captopril on ACE

Captopril is prepared with ultrapure water in 2 mg/mL, and then diluted with ultrapure water in 10-time proportion (till $10^{-8}$).

Preparation for the reaction system is shown in the following table:

|  | No. | | | | | |
| --- | --- | --- | --- | --- | --- | --- |
|  | 1 | 2 | 3 | 4 | 5 | 6 |
| FAPGG reagent (μl) | 200 | 200 | 200 | 200 | 200 | 200 |
| 115 u/L ACE (μl) | 20 | 20 | 20 | 20 | 20 | 20 |
| 2 μg/L Captopril (μl) | 20 | 16 | 12 | 8 | 4 | 0 |
| Ultrapure water (μl) | 0 | 4 | 8 | 12 | 16 | 20 |
| FAPGG reagent (μl) | 200 | 200 | 200 | 200 | 200 | 200 |
| 115 u/L ACE (μl) | 20 | 20 | 20 | 20 | 20 | 20 |
| 0.2 μg/L Captopril (μl) | 20 | 16 | 12 | 8 | 4 | 0 |
| Ultrapure water (μl) | 0 | 4 | 8 | 12 | 16 | 20 |

The substances are mixed and placed in a SpectraMax microplate reader to determine change of absorbance value with 340 nm as a main wavelength and 405 nm as a reference wavelength at 37° C., and continuously monitored for 1 hour.

Figure 3:
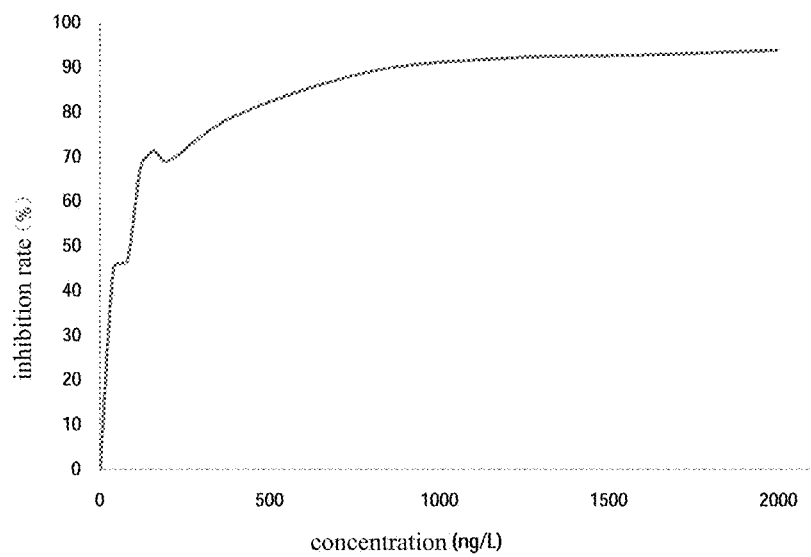
FIG. 3 is an ACE inhibition curve with Captopril.

The inhibition curve with Captopril is shown in FIG. 3. It can be seen from FIG. 3 that, viewed from the overall trend, the inhibition rate is decreased as the concentration of Captopril decreases. Since the concentrations are in linear in the experiment, the variation range of the inhibition rate is reduced.

Inhibitory Effect of Dipeptides on ACE

20 μg/mL stock solution is prepared by dissolving synthetic dipeptide samples in ultrapure water. The stock solution is then diluted to a 20 μg/mL sample as test sample.

|  | No. | | | | | |
| --- | --- | --- | --- | --- | --- | --- |
|  | 1 | 2 | 3 | 4 | 5 | 6 |
| FAPGG reagent (μl) | 200 | 200 | 200 | 200 | 200 | 200 |
| 115 u/L ACE (μl) | 20 | 20 | 20 | 20 | 20 | — |
| 20 μg/mL dipeptide (μl) | 20 | — | — | — | — | — |
| Captopril (μl) | — | 4 | 20 | 20 | — | — |
| Ultrapure water (μl) | 0 | 16 | 0 | 0 | 20 | 40 |

The substances are mixed and placed in a SpectraMax microplate reader to determine change of absorbance value with 340 nm as a main wavelength and 405 nm as a reference wavelength at 37° C., and continuously monitored for 1 hour. The slopes of linear segment of the enzymatic kinetic curve are calculated, and the inhibition rates of the samples are calculated according to formula (1);

$$\text{Inhibition rate } (\%) = \frac{115 - E}{115} \times 100$$

-continued

Wherein, $E = \dfrac{S_s - S_b}{S_p - S_b} \times 115$

E-ACE enzyme activity in a sample well
$S_s$-slope of linear segment of ACE kinetic curve for a sample well
$S_p$-slope of linear segment of ACE kinetic curve for a well without inhibitor
$S_b$-slope of linear segment of ACE kinetic curve for a blank well The experimental results are shown in the following table:

| No. | Dipeptide | Inhibition rate (%) |
|---|---|---|
| 3 | FE | 6.18 |
| 5 | KW | 16.42 |
| 9 | IF | 18.35 |
| 11 | KY | 11.54 |
| 13 | AY | 8.18 |
| 15 | KP | 7.88 |
| 19 | WL | 7.27 |
| 20 | KA | 6.45 |
| 22 | AG | 3.08 |
| 25 | CA | 84.38 |
| 28 | CH | 70.79 |
| 29 | CI | 67.52 |
| 30 | CK | 38.39 |
| 38 | DE | 15.16 |
| 47 | EV | 14.26 |
| 48 | EW | 9.91 |
| 49 | FD | 5.05 |
| 50 | FH | 10.06 |
| 51 | FI | 9.58 |
| 55 | FQ | 10.96 |
| 57 | FT | 1.92 |
| 58 | FW | 3.16 |

-continued

| No. | Dipeptide | Inhibition rate (%) |
|---|---|---|
| 59 | GC | 0.12 |
| 64 | GT | −3.20 |
| 65 | HC | 5.06 |
| 66 | HD | 10.98 |
| 67 | HE | 9.95 |
|  | Cap1 | 86.95 |
|  | Cap2 | 72.84 |
|  | Cap3 | 35.84 |

It can be seen from the table that when the N-terminal of a dipeptide is a cysteine, the ACE inhibition rate of the dipeptide is significantly higher than those of other dipeptides; and more particularly, when the dipeptide is CA, CH, CI or CK, the inhibition rate is even higher.

The invention claimed is:

1. A method of inhibiting an ACE enzyme by exposing the ACE enzyme to an ACE enzyme activity inhibitor, wherein the ACE enzyme activity inhibitor is a dipeptide, wherein said dipeptide is selected from the group consisting of CA, CH, CI, or CK;
   the N-terminal of the dipeptide is a cysteine, the amino acid in the dipeptide is in L-form or D-form, and at least one amino acid in the dipeptide is optionally modified with a group which can improve the stability of the dipeptide in vivo;
   wherein the C-terminal amino acid of the dipeptide is a basic amino acid or an aliphatic amino acid;
   wherein the basic amino acid is H or K; and
   wherein the aliphatic amino acid is A or I.

2. The method according to claim 1, wherein the ACE enzyme activity inhibitor is administered to a patient to lower blood pressure.

* * * * *